United States Patent [19]

Large et al.

[11] 4,191,552
[45] Mar. 4, 1980

[54] AMINE SALTS OF SUBSTITUTED N-PHOSPHONOMETHYLUREAS AND THEIR USE AS PLANT GROWTH REGULATORS

[75] Inventors: George B. Large, Orinda; Lawrence Buren, Cupertino, both of Calif.

[73] Assignee: Stauffer Chemical Company, Westport, Conn.

[21] Appl. No.: 8,719

[22] Filed: Feb. 2, 1979

[51] Int. Cl.² .................... A01N 5/00; C07C 101/24
[52] U.S. Cl. ........................... 71/86; 560/169; 71/71; 71/78
[58] Field of Search ............... 71/86, 71, 76; 260/938; 562/560; 560/169

[56] References Cited

U.S. PATENT DOCUMENTS

| | | | |
|---|---|---|---|
| 3,853,530 | 12/1974 | Franz | 71/76 |
| 4,130,412 | 12/1978 | Franz | 71/86 |

*Primary Examiner*—Catherine L. Mills

*Attorney, Agent, or Firm*—M. Henry Heines

[57] ABSTRACT

Novel amine salts of substituted N-phosphonomethylureas are disclosed herein, having the formula

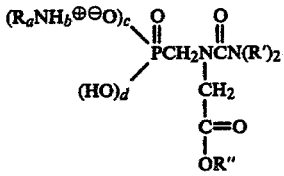

in which
R, R', and R" are independently $C_1$–$C_4$ alkyl;
a is 1 or 2 and b is 2 or 3, such that the sum of a and b is 4; and
c is 1 or 2 and d is 0 or 1, such that the sum of c and d is 2.

The compounds are useful in regulating the natural growth or development of plants.

27 Claims, No Drawings

AMINE SALTS OF SUBSTITUTED N-PHOSPHONOMETHYLUREAS AND THEIR USE AS PLANT GROWTH REGULATORS

BRIEF DESCRIPTION OF THE INVENTION

This invention resides in novel amine salts of substituted N-phosphonomethylureas, their use in regulating the natural growth or development of plants, and biologically active compositions containing these compounds together with an inert diluent carrier. In particular, this invention relates to the chemical treatment of plants with the result of altering their natural growth or development such that various agricultural or horticultural features of the plants are enhanced. As employed herein, the term "natural growth or development" designates the normal life cycle of a plant in accordance with its genetics and environment, in the absence of artificial external influences. A particularly preferred utility of the instant compounds is in increasing the sucrose yield of field grown sugarcane and sorghum.

The compounds of the present invention are represented by the formula

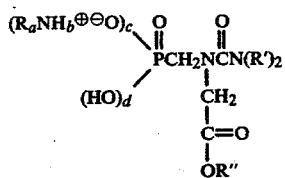

in which

R, R', and R" are independently $C_1$–$C_4$ alkyl;

a is 1 or 2 and b is 2 or 3, such that the sum of a and b is 4; and c is 1 or 2 and d is 0 or 1, such that the sum of c and d is 2.

The term "alkyl" is used herein to include both straight-chain and branched-chain alkyl groups. The carbon atom range is intended to be inclusive of its upper and lower limits.

Within the scope of the above formula, certain embodiments are preferred. Specifically, R is preferably isopropyl, R' is preferably methyl or ethyl, and R" is preferably ethyl. While the present invention is intended to cover both mono-salts, where c and d are both 1, and di-salts, where c is 2 and d is 0, the former are preferred over the latter where bulky amines are used which sterically hinder complete neutralization.

DETAILED DESCRIPTION OF THE INVENTION

In accordance with the instant invention it has been found that desirable regulation of the natural growth or development of plants is achieved by the application of a compound within the above formula directly to the plants or to any of their above-ground portions at approximately 4 to 10 weeks prior to harvest. Application of the compound to the plant is achieved with a growth regulating effect, but without herbicidal results. While the compound can be applied in an amount sufficient to kill certain plants, it is contemplated herein to employ only such amounts as will serve to regulate the natural growth and development. As understood by those skilled in the art, such effective plant regulating amounts vary, not only with the particular material selected for treatment, but also with the regulatory effect to be achieved, the species of plant being treated and its stage of development, and whether a permanent or transient regulating effect is sought. Other factors which may bear upon the determination of an appropriate plant regulating amount include the manner in which the treatment is to be applied, weather conditions such as temperature or rainfall, and the like.

Regulation of the natural growth or development of plants by chemical treatment may result from the effect of the chemical substance on the physiological processes of the plants, or it may be due to the effect of such substance on the morphology of the plant. Such regulation may also result from both physiological and morphological effects in combination or sequence.

In general, regulation of the natural growth or development which leads to a morphological change in the plant is readily noticeable by visual observation. Such changes can be found in the size, shape, color or texture of the treated plant or any of its parts. Similarly, changes in the quantity of plant fruit or flowers can be simply noted.

On the other hand, regulation which leads to changes in the physiological processes occur within the treated plant and are usually hidden from the eye of an observer. Changes of this type are most often in the production, location, storage or use of naturally occurring chemicals, including hormones, within the plant. Physiological changes in a plant may be recognized when followed by a subsequent change in morphology. Additionally, there are numerous analytical procedures known to those skilled in the art for determining the nature and magnitude of changes in the various physiological processes.

The individual compounds of the instant invention serve to regulate the natural growth or development of treated plants in a number of diverse ways, and it is to be understood that each compound may not produce identical regulatory effects on each plant species or at every rate of application. As stated above, responses will vary in accordance with the compound, the rate, the plant, etc.

Among the particular regulatory responses demonstrated by compounds of this invention is defoliation. Defoliation is not a herbicidal action. Indeed, killing of the treated plant is undesirable since leaves will continue to adhere to a dead plant. Rather, it is necessary that the plant remain alive while the leaves separate and fall away. This permits further development of the productive plant parts, and inhibits further leaf growth. As a result, other parts of the plant demonstrate extra growth, and subsequent harvesting operations are facilitated. Defoliants are useful in crops such as flax, cotton, beans and the like.

Another regulatory response demonstrated by compounds of this invention is the retardation of vegetative growth in general. Such a response has a wide variety of beneficial features. In certain plants this retardation causes a diminution or elimination of the normal apical dominance leading to a shorter main stem and increased lateral branching. This alteration of the natural growth or development produces smaller, bushier plants which often demonstrate increased resistance to drought and pest infestation.

In the case of turf grasses retardation of vegetative growth is also highly desirable. When the vertical growth of such grasses is slowed, it is found that root development is enhanced to provide a dense, sturdier turf. Naturally, such retardation of turf grasses also serves to increase the interval between mowings of lawns, golf courses and similar grassy areas.

In many types of plants, such as silage crops, potatoes, sugar cane, beets, grapes, melons and fruit trees, the retardation of vegetative growth caused by compounds of this invention results in an increase in the carbohydrate content of the plants at harvest. It is believed that by retarding or suppressing such growth at the appropriate stage of development, less of the available carbohydrate is consumed for vegetative growth with a consequent enhancement of the starch and/or sucrose content.

Retardation of vegetative growth in fruit trees is demonstrated by shorter branches which lead to more fullness in shape and may also result in lesser vertical elongation. These factors contribute to the ease of access to the orchard and simplify the fruit harvesting procedure.

As illustrated in the examples which are hereinafter presented, the individual compounds of the invention regulate the natural growth or development of treated plants in numerous other and different respects. Although regulatory effects themselves are often desirable in their own right, it is most often the ultimate result of these effects upon the economic factor which is of primary significance. Thus, it must be recognized that increases in the yield of individual plants, increases in the yield per unit area, and reductions in the cost of harvesting and/or subsequent processing are all to be considered in any assessment of the consequence of an individual regulatory effect during the growth or development of a plant.

The specific examples which follow are presented as merely illustrative, non-limiting demonstrations of the preparation of the compounds of the instant invention and of their effectiveness in regulating the growth of plants.

EXAMPLE I

This example illustrates the preparation of one of the compounds of the present invention, the mono(diisopropylamine) salt of N,N-dimethyl-N'-carboethoxymethyl-N'-phosphonomethylurea. The preparation is shown in three steps, beginning with the chloromethylation of N,N-dimethyl-N'-carboethoxymethylurea, followed by an Arbusov reaction with trimethylphosphite, and conversion of the resulting phosphonate ester to the corresponding phosphonic acid which is subsequently neutralized with diisopropylamine. The product isolated from the neutralization with excess diisopropylamine was the mono-amine salt.

1. Preparation of N,N-Dimethyl-N'-carboethoxymethyl-N'-chloromethylurea

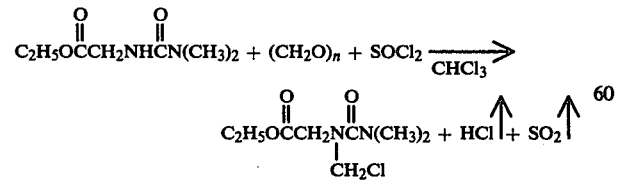

A reaction flask was charged with 100 cubic centimeters (cc) of chloroform, 45.4 grams (g) (0.26 mole) of N,N-dimethyl-N'-carboethoxymethylurea, and 9.0 g (0.3 mole) of paraformaldehyde. While the mixture was stirred continuously at room temperature, 35.4 g (21.4 cc, 0.3 mole) of thionyl chloride in a concentrated chloroform solution was added dropwise. A rise in temperature to 34° C. was observed. Hydrogen chloride and sulfur dioxide gases evolving from the reaction mixture were trapped in a caustic solution. The product was isolated by evaporation of the solvent, to provide 53.4 g, representing essentially full conversion. The structure as shown above was confirmed by proton resonance and mass spectrometry. The refractive index of the product was $n_D^{30} = 1.4782$.

2. Preparation of N,N-Dimethyl-N'-carboethoxymethyl-N'-(O,O-dimethylphosphonomethyl)urea

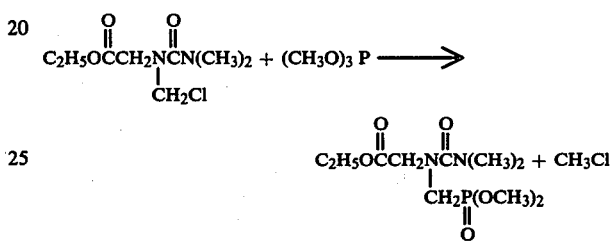

A reaction flask was charged with 31.9 g (0.14 mole) of N,N-dimethyl-N'-carboethoxymethyl-N'-chloromethylurea and 22.0 g (0.2 mole) of trimethylphosphite. After a mild rise in temperature, the reaction mixture was stirred for 30 minutes at room temperature, followed by one hour at 50° C. The product was isolated by evaporation to produce a crude yield of 43.6 g. The structure shown above was confirmed by proton resonance and mass spectrometry, with refractive index $n_D^{30} = 1.4642$.

3. Preparation of Mono(diisopropylamine) Salt of N,N-Dimethyl-N'-carboethoxymethyl-N'-phosphonomethylurea

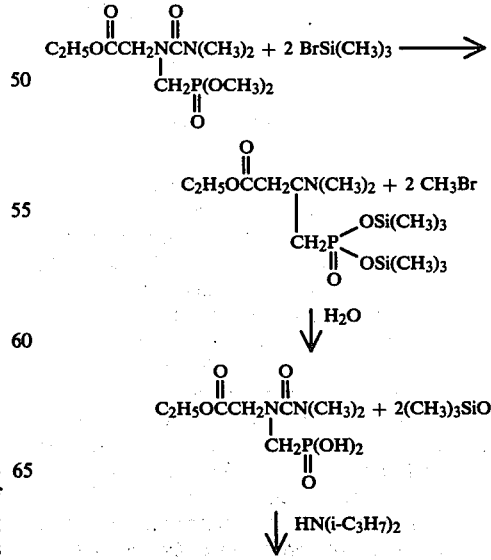

-continued

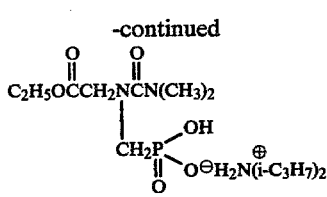

The phosphonate ester of the previous step (5.9 g, 0.020 mole) was placed under nitrogen and treated with 6.1 g (0.056 mole) of bromotrimethylsilane at 5° C. The mixture was stirred for one hour at room temperature, and then poured into water. An insoluble oil formed and separated, weighing 5.4 g. A portion was treated with an excess of diisopropylamine. The salt thus formed had a melting point of 164°–165° C., and was determined by carbon-13 resonance spectrometry to be the mono(diisopropylamine) salt of N,N-dimethyl-N'-carboethoxymethyl-N'-phosphonomethylurea.

Similar procedures were employed using monoisopropylamine in place of the diisopropylamine in the last step of Example I. The monoisopropylamine formed di-salts as follows:

Di(monoisopropylamine) salt of N,N-dimethyl-N'-carboethoxymethyl-N'-phosphonomethylurea: melting point range 105°–107° C.

Di(monoisopropylamine) salt of N,N-diethyl-N'-carboethoxymethyl-N'-phosphonomethylurea: melting point range 95°–99° C.

Other compounds within the scope of the generic formula shown above can be similarly prepared with appropriate starting materials.

EXAMPLE II

This example illustrates the utility of three of the compounds of the present invention in the growth regulation of sweet sorghum (scientific name: *Sorghum vulgare*). The compounds tested were as follows:

| Compound | Name |
|---|---|
| A | Mono(diisopropylamine) salt of N,N-dimethyl-N'-carboethoxymethyl-N'-phosphonomethylurea |
| B | Di(monoisopropylamine) salt of N,N-dimethyl-N'-carboethoxymethyl-N'-phosphonomethylurea |
| C | Di(monoisopropylamine) salt of N,N-diethyl-N'-carboethoxymethyl-N'-phosphonomethylurea |

The following test procedure was used:

A series of white plastic pots, 7.5 inches (19.0 cm) in diameter, were filled with approximately 10 pounds (4.54 kilograms) each of sandy loam soil containing 100 parts per million (ppm) of cis-N-[(trichloromethyl)thio]-4-cyclohexene-1,2-dicarboximide (a commercially available fungicide) and 150 ppm of 17-17-17 fertilizer (i.e., comprising 17% by weight each of N, $P_2O_5$, and $K_2O$). Eight sorghum seeds were placed in each pot and the pots were placed in a greenhouse in which the temperature was maintained at 27° C. during the day and 21° C. at night. During the next five weeks, the emerging plants were thinned down to one per pot. The pots were fertilized periodically with 17-17-17 fertilizer.

Approximately two weeks prior to the emergence of the seedheads, the plants were sprayed with solutions of the test compounds dissolved in equal proportions of acetone and water. The spraying system was pressurized by carbon dioxide and mounted on a bicycle-type apparatus. The test solutions were applied at a rate of 80 gallons per acre (750 liters per hectare). The concentrations of the solutions were predetermined to produce the desired application rates in pounds per acre (lb/A) with this volumetric application rate, i.e., 2 lb/A (2.2 kilograms per hectare) and 4 lb/A (4.5 kilograms per hectare).

Following treatment, the plants were placed in the greenhouse for an additional six weeks. During this time, the degree of seedhead emergence and pollen shedding were recorded periodically.

Approximately fourteen weeks after the seeds were planted, the plants were harvested. The stalks were cut at soil level and the seedhead and peduncle were removed. For each stalk, the seedhead was weighed (fresh weight), then dried and re-weighed (dry weight), and the peduncle length was measured. The remainder of the stalk was then stripped of all leaves and leaf sheaths, and its length and weight were determined. The stalk was then chopped into small segments and squeezed in a hydraulic press at a pressure of 20,000 pounds per square inch (13,800 Newtons per square centimeter). The quantity of the expressed juice was measured as well as its quality in terms of total dissolved solids. The latter was measured with a hand juice refractometer, and is expressed as weight percent of the juice.

Six replications were performed on each test compound at each application rate. In addition, six untreated plants were included as check plants for comparison. The results are shown in Tables 1 and 2.

Table 1 lists the data pertaining to seedhead emergence and pollen shedding. The data listed are averages of each set of six replications. It is clear in each case that the extent of seedhead emergence and pollen shedding was reduced when the test compounds were applied, particularly at 82, 84, and 86 days after the seeds were first planted. This reduction in flowering is one indication of an increase in the efficiency of sucrose production and storage.

Table 2 lists averages of the measurements taken on the seedhead, peduncle, stalk, and expressed juice after the harvesting of the plants. The data indicates a reduction in seedhead fresh and dry weights and peduncle lengths, and an increase in the percentage of total dissolved solids in the expressed juice in each case where a test compound was applied.

TABLE 1

PRE-HARVEST DATA AVERAGES
Seedhead Emergence (%) and Pollen Shed (%)

| Test Compound (Rate) | DAYS AFTER SEEDING | | | | | | | |
|---|---|---|---|---|---|---|---|---|
| | 82 | | 84 | | 86 | | 89 | |
| | SHE | PS | SHE | PS | SHE | PS | SHE | PS |
| NONE | 70 | 47 | 85 | 73 | 88 | 82 | 100 | 100 |
| A (2 lb/A) | 4 | 0 | 6 | 0 | 6 | 0 | 8 | 0 |
| A (4 lb/A) | 0 | 0 | 0 | 0 | 0 | 0 | 0 | 0 |
| B (2 lb/A) | 2 | 0 | 2 | 0 | 2 | 0 | 2 | 0 |
| C (2 lb/A) | 38 | 15 | 62 | 37 | 74 | 48 | 100 | 95 |
| C (4 lb/A) | 24 | 4 | 73 | 39 | 86 | 54 | 100 | 96 |

SHE : Seedhead Emergence
PS : Pollen Shedding

TABLE 2
POST-HARVEST DATA AVERAGES

| Test Compound (Rate) | Seedhead FW (g) | Seedhead DW (g) | Peduncle Length (mm) | Stalk Height (mm) | Stalk FW (g) | Expressed Juice Amount (g) | Expressed Juice TDS (wt %) |
|---|---|---|---|---|---|---|---|
| NONE | 75 | 35.0 | 336 | 1728 | 352 | 141 | 11.4 |
| A (2 lb/A) | 2 | 1.0 | 23 | 1142 | 259 | 77 | 16.2 |
| A (4 lb/A) | 0 | 0 | 9 | 1003 | 255 | 77 | 16.1 |
| B (2 lb/A) | 1 | 0 | 30 | 996 | 298 | 87 | 18.9 |
| C (2 lb/A) | 56 | 22.3 | 315 | 1681 | 364 | 149 | 12.6 |
| C (4 lb/A) | 62 | 24.8 | 311 | 1730 | 347 | 143 | 13.3 |

FW : Fresh Weight
DW : Dry Weight
TDS : Total Dissolved Solids

EXAMPLE III

A procedure similar to that described in Example II was used to further evaluate the growth regulation properties of Compounds A and B. In these experiments, however, the plants were more mature when sprayed with the test chemicals, i.e., the seedheads were just starting to emerge and the plants were harvested after 20 weeks rather than 14. Nevertheless, growth regulating effectiveness was observed in essentially the same manner as in Example II, as indicated by Tables 3 and 4.

TABLE 3

Pre-Harvest Data - Averages of Six Replications
Seedhead Emergence (%) and Pollen Shed (%)

| Test Compound (Rate) | Days After Seeding 108 SHE | 108 PS | 112 SHE | 112 PS | 119 SHE | 119 PS |
|---|---|---|---|---|---|---|
| NONE | 55.0 | 39.5 | 90.6 | 77.5 | 98.7 | 98.7 |
| A (0.25 lb/A) | 65.0 | 35.6 | 97.5 | 90.0 | 98.1 | 98.1 |
| A (0.5 lb/A) | 50.6 | 34.3 | 85.6 | 71.2 | 97.5 | 97.5 |
| A (1.0 lb/A) | 76.8 | 41.2 | 95.6 | 93.1 | 96.8 | 96.8 |
| B (0.25 lb/A) | 0 | 0 | 26.8 | 11.8 | 100.0 | 98.7 |
| B (0.5 lb/A) | 16.2 | 31.0 | 54.3 | 37.5 | 89.3 | 86.8 |
| B (1.0 lb/A) | 16.2 | 6.8 | 38.1 | 25.6 | 70.6 | 60.2 |

SHE : Seedhead Emergence
PS : Pollen Shedding

TABLE 4
POST-HARVEST DATA - AVERAGES OF SIX REPLICATIONS

| Test Compound (Rate) | Seedhead FW (g) | Seedhead DW (g) | Peduncle Length (mm) | Stalk Height (mm) | Stalk FW (g) | Expressed Juice Amount (g) | Expressed Juice TDS (wt %) |
|---|---|---|---|---|---|---|---|
| NONE | 74.4 | 46.2 | 311 | 1180 | 203 | 87.6 | 9.6 |
| A (0.25 lb/A) | 80.5 | 50.4 | 267 | 1241 | 193 | 77.3 | 8.2 |
| A (0.5 lb/A) | 64.4 | 41.2 | 269 | 1291 | 189 | 73.8 | 11.4 |
| A (1.0 lb/A) | 56.1 | 38.1 | 250 | 1244 | 171 | 65.6 | 15.8 |
| B (0.25 lb/A) | 67.0 | 36.8 | 302 | 1489 | 201 | 77.3 | 13.7 |
| B (0.5 lb/A) | 53.5 | 32.1 | 225 | 1326 | 162 | 60.8 | 12.0 |
| B (1.0 lb/A) | 40.6 | 24.8 | 168 | 1299 | 186 | 64.8 | 14.7 |

FW : Fresh Weight
DW : Dry Weight
TDS : Total Dissolved Solids

METHODS OF APPLICATION

The plant-regulating compositions of the present invention are most useful when applied directly to the plants subsequent to their emergence from the soil. When applied in such a manner, the compositions are generally embodied in formulations suitable for convenient application. Typical formulations contain additional ingredients or diluent carriers which are either inert or active. Examples of such ingredients or carriers are water, organic solvents, oil and water, water-oil emulsions, wetting agents, dispersing agents, and emulsifying agents. The formulations generally take the form of dusts, solutions, emulsifiable concentrates, or wettable powders.

A. Dusts

Dusts are dense powder compositions which are intended for application in dry form. Dusts are characterized by their free-flowing and rapid settling properties so that they are not readily windborne to areas where their presence is not desired. They contain primarily an active material and a dense, free-flowing, solid carrier. Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of inert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease in incorporation some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diatomaceous silica, synthetic fine silica and synthetic calcium and magnesium silicates.

Most preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentration of up to about 0.5 weight percent, and minor amounts of anticaking and antistatic agents. The particle size of the carrier is usually in the range of 30 to 50 microns.

B. Solutions

Liquid solutions of the active compounds are the preferred formulations for the purposes of the instant invention. Water is the preferred carrier. The active compounds are dissolved in water such that application at the rate of about 1 to about 200 gallons of solution per acre (about 9 to about 1875 liters per hectare) will provide the required amount of active ingredient.

Typical solutions for such use also contain a small amount of non-phytotoxic surfactant to improve the wetting ability of the solution and thus its distribution over the plant surface. The surfactant is normally used in an amount ranging from about 0.01% by weight to about 5% by weight with respect to the water, preferably from about 0.05% by weight to about 0.5% by weight.

The surfactants for use as described above can be anionic, cationic, nonionic, ampholytic and zwitterionic types.

Examples of suitable anionic surfactants for use herein are the alkali metal (for example, sodium) ammonium and amine salts of fatty alcohol sulfates having from 8-18 carbon atoms in the fatty chain and sodium salts of alkyl benzene sulfonates having from 9 to 15 carbon atoms in the alkyl chain.

Examples of suitable cationic surfactants are dimethyl dialkyl quaternary ammonium salts wherein the alkyl chains contain from about 8 to 18 carbon atoms and the salt forming anion is a halogen.

Examples of suitable nonionic surfactants are the polyoxyethylene adducts of fatty alcohols having 10 to 18 carbon atoms, and the polyethylene oxide condensates of alkyl phenols wherein the alkyl chain contains from about 6 to 12 carbon atoms and the amount of ethylene oxide condensed onto each mole of alkyl phenol is from about 5 to 25 moles, and the polyethylene oxide condensates of sorbitan esters wherein the amount of ethylene oxide condensed onto each mole of sorbitan ester is about 10 to 40 moles.

Examples of suitable ampholytic surfactants are derivatives of aliphatic secondary or tertiary amines in which one of the aliphatic substituents contains from about 8 to 18 carbon atoms and one contains an anionic water solubilizing group, e.g., sulfate or sulfonate. Specific suitable ampholytic surfactants are sodium-3-dodecylaminopropionate and sodium-3-dodecyl amino propane sulfonate.

Examples of suitable zwitterionic surfactants are derivatives of aliphatic quaternary ammonium compounds in which one of the aliphatic constituents contains from about 8 to 18 carbon atoms and one contains an anionic water solubilizing group. Specific examples of zwitterionic surfactants are 3-(N,N-dimethyl-N-hexadecylammonio)propane-1-sulfonate and 3-(N,N-dimethyl-N-hexadecylammonio)-2-hydroxy propane-1-sulfonate.

C. Emulsifiable Concentrates

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohols sulfates, oil soluble petroleum sulfonates or, preferably, mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

D. Wettable Powders

Wettable powders are water-dispersible compositions containing the active material, an inert solid extender, and one or more surfactants to provide rapid wetting and prevent heavy flocculation when suspended in water.

The inert solid extenders are usually of mineral origin such as the natural clays, diatomaceous earth and synthetic minerals derived from silica and the like. Examples of such extenders include kaolinites, attapulgite clay, montmorillonite clays, synthetic silicas, synthetic magnesium silicate and calcium sulfate dihydrate.

Suitable surfactants for use in such compositions include both the nonionic and anionic type, and those most suitable for the preparation of the dry, wettable products of this invention are solid forms of compounds known to the art as wetters and dispersants. Occasionally a liquid, nonionic compound classified primarily as an emulsifier may serve as both wetter and dispersant.

Most preferred wetting agents are alkylbenzene and alkylnaphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

Wetting and dispersing agents in these preferred wettable powder compositions of this invention are usually present at concentrations of from about 0.5 weight percent to 5 weight percent. The inert extender then completes the formulation. Where needed, 0.1 weight percent to 1.0 weight percent of the extender may be replaced by a corrosion inhibitor or an antifoaming agent or both.

Thus, wettable powder formulations of the invention will contain from about 25 to 90 weight percent active material, from 0.5 to 2.0 weight percent wetting agent, from 0.25 to 5.0 weight percent dispersant, and from 9.25 to 74.25 weight percent inert extender, as these terms are described above.

When the wettable powder contains a corrosion inhibitor or an antifoaming agent or both, the corrosion inhibitor will not exceed about 1 percent of the composition and the antifoaming agent will not exceed about 0.5 percent by weight of the composition, both replacing equivalent amounts of the inert extender.

E. In General

In general, any conventional method of application can be used. Dusts and liquid compositions can be applied by the use of powder dusters, boom and hand sprayers, and spray dusters. The compositions can also be applied from airplanes as dusts or sprays because they are effective in very low dosages.

The compositions of the present invention can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the active compound in the irrigation water will range from about 10 to 150 parts per million by weight. The irrigation water is preferably applied by the use of sprinkler systems. Such application is most effectively done about 4 to 10 weeks prior to harvest.

The amount of composition of the present invention which constitutes an effective, plant-regulating, nonlethal amount depends upon the nature of the plants to be controlled. The rate of application of active ingredients varies from about 0.1 to about 20 pounds per acre (lb/A) (0.11 to 22 kilograms per hectare, kg/ha), preferably about 0.1 to about 10 lb/A (0.11 to 11 kg/ha), most preferably about 0.5 to about 8 lb/A (0.56 to 9.0 kg/ha), with the actual amount used depending on the overall cost and the desired results. It will be readily apparent to one skilled in the art that compositions exhibiting lower plant regulating activity will require a higher dosage rate for the same degree of control than more active compounds.

What is claimed is:

1. A compound having the formula

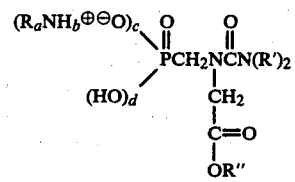

in which
R, R', and R'' are independently $C_1$–$C_4$ alkyl;
a is 1 or 2 and b is 2 or 3, such that the sum of a and b is 4; and
c is 1 or 2 and d is 0 or 1, such that the sum of c and d is 2.

2. A compound according to claim 1 in which R is isopropyl.
3. A compound according to claim 1 in which R' is methyl or ethyl.
4. A compound according to claim 1 in which R'' is ethyl.
5. A compound according to claim 1 in which R is isopropyl, R' is methyl or ethyl, and R'' is ethyl.
6. A compound according to claim 1 in which R is isopropyl, R' is methyl, and R'' is ethyl.
7. A compound according to claim 1 in which R is isopropyl, R' is methyl, R'' is ethyl, a is 2, b is 2, c is 1, and d is 1.
8. A compound according to claim 1 in which R is isopropyl, R' is methyl, R'' is ethyl, a is 1, b is 3, c is 2, and d is 0.
9. A compound according to claim 1 in which R is isopropyl, R' is ethyl, R'' is ethyl, a is 1, b is 3, c is 2, and d is 0.
10. A biologically active composition comprising an effective plant-regulating, non-lethal amount of a compound having the formula

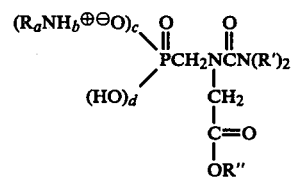

in which
R, R', and R'' are independently $C_1$–$C_4$ alkyl;
a is 1 or 2 and b is 2 or 3, such that the sum of a and b is 4; and
c is 1 or 2 and d is 0 or 1, such that the sum of c and d is 2;
and an inert diluent carrier.

11. A composition according to claim 10 in which R is isopropyl.
12. A composition according to claim 10 in which R' is methyl or ethyl.
13. A composition according to claim 10 in which R'' is ethyl.
14. A composition according to claim 10 in which R is isopropyl, R' is methyl or ethyl, and R'' is ethyl.
15. A composition according to claim 10 in which R is isopropyl, R' is methyl, and R'' is ethyl.
16. A composition according to claim 10 in which R is isopropyl, R' is methyl, R'' is ethyl, a is 2, b is 2, c is 1, and d is 1.

17. A composition according to claim 10 in which R is isopropyl, R' is methyl, R" is ethyl, a is 1, b is 3, c is 2, and d is 0.

18. A composition according to claim 10 in which R is isopropyl, R' is ethyl, R" is ethyl, a is 1, b is 3, c is 2, and d is 0.

19. A method of regulating the natural growth and development of plants which comprises applying to said plants a biologically active composition comprising an effective, plant-regulating, non-lethal amount of a compound having the formula

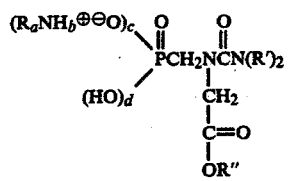

in which

R, R', and R" are independently $C_1$–$C_4$ alkyl;

a is 1 or 2 and b is 2 or 3, such that the sum of a and b is 4; and c is 1 or 2 and d is 0 or 1, such that the sum of c and d is 2;

and an inert diluent carrier.

20. A method according to claim 19 in which R is isopropyl.

21. A method according to claim 19 in which R' is methyl or ethyl.

22. A method according to claim 19 in which R" is ethyl.

23. A method according to claim 19 in which R is isopropyl, R' is methyl or ethyl, and R" is ethyl.

24. A method according to claim 19 in which R is isopropyl, R' is methyl, and R" is ethyl.

25. A method according to claim 19 in which R is isopropyl, R' is methyl, R" is ethyl, a is 2, b is 2, c is 1, and d is 1.

26. A method according to claim 19 in which R is isopropyl, R' is methyl, R" is ethyl, a is 1, b is 3, c is 2, and d is 0.

27. A method according to claim 19 in which R is isopropyl, R' is ethyl, R" is ethyl, a is 1, b is 3, c is 2, and d is 0.

* * * * *